United States Patent [19]

Acharya

[11] Patent Number: 5,336,486
[45] Date of Patent: Aug. 9, 1994

[54] APPETITE CONTROL METHOD

[75] Inventor: Ramesh N. Acharya, Lake Forest, Ill.

[73] Assignee: TheraTech, Inc., Salt Lake City, Utah

[21] Appl. No.: 676,328

[22] Filed: Mar. 28, 1991

[51] Int. Cl.$^5$ .......................... A61K 31/74; A61K 9/20
[52] U.S. Cl. ................................ 424/78.01; 424/464; 514/909; 514/911
[58] Field of Search .............................. 424/468, 78.01; 514/909, 911, 960; 426/464

[56] References Cited

U.S. PATENT DOCUMENTS 4,869,908  9/1989  Kirschner et al. .................. 424/468

Primary Examiner—Marianne M. Cintins
Assistant Examiner—K. Weddington
Attorney, Agent, or Firm—Morrison & Foerster

[57] ABSTRACT

A method for suppressing appetite comprising administering by mouth to a subject an amount of polycarbophil that is effective to suppress the appetite of the subject without inducing a laxative effect in said subject.

14 Claims, No Drawings ly Control Method

APPETITE CONTROL METHOD

SUMMARY OF THE INVENTION

This invention relates to the field of weight-loss, generally, and in particular to compositions that suppress appetite and/or promote a feeling of satiation.

BACKGROUND OF THE INVENTION

It is well recognized that for hundreds of years mankind has struggled to maintain or achieve a body weight that is concurrently healthy and appealing. This is a battle that is rarely won because human physiology causes the generation of "hunger" pains when in fact there is no eminent need to eat, probably a carry-over from the primal days when man needed to eat substantial quantities of food when it was available, to last until the next food could be obtained, as through hunting, trapping, and the like.

Unfortunately, because mankind suffers from unnecessary "hunger" pains or at least unnecessary urges to eat, when food is not really necessary, and due to the fact that food in most countries is readily available on an almost constant basis, body weight is allowed to increase beyond the point necessary to maintain good health and in fact becomes, in many instances, a health risk. The problem is how to reduce food intake, while eliminating these primal hunger pains or urges to eat, to allow reduced food intake or dieting to control body weight.

Although many attempts have been made to cause one to feel "full" or satiated, when the stomach is not in fact filled with food, such as by filling the stomach with fiber or other low or no-calorie materials, each solution to date has had its own problems. For example, if one intakes substantial amounts of fiber, that also requires that one expel large quantities, as well, causing man to suffer gastrointestinal discomfort. Others cannot tolerate such high volumes of fiber, and the like, for other reasons.

Another approach has been the use of chemical appetite suppressants. Although such suppressants exist, they either do not cause a true feeling of satiation to exist, such as that brought on by a "full" stomach, or they cause undesirable side-effects, such as anxiety, hyperactivity, or the like.

What has been needed, heretofore, but has not been achievable is a low-bulk material which suppresses appetite and causes one to feel satiated, without causing undesirable side-effects.

SUMMARY OF THE INVENTION

There has now been discovered that polycarbophil, when ingested in controlled quantities, suppresses appetite and causes a feeling of satiation, such as that caused by a "full" stomach. Accordingly, the ingestion of from about 0.010 to about 0,500 grams of calcium polycarbophil causes a feeling of satiation in the human and the ingestion of such a quantity of calcium polycarbophil, specifically prior to regular meals, on a routine basis is an effective means of appetite suppression and weight control.

DETAILED DESCRIPTION OF THE PREFERRED EMBODIMENTS

As indicated, it has now been surprisingly discovered that polycarbophil, when administered in an effective amount, acts to both suppress appetite and to induce a feeling of satiation. Polycarbophil can be administered as such or, preferably, in the form of a pharmaceutically acceptable salt. Most preferably the polycarbophil is administered in the form of calcium polycarbophil.

Several types of materials are suitable for forming the polycarbophil type composition component. The polymer contains a plurality of a repeating unit of which at least about 80 percent contain at least one carboxyl functionality and about 0.05 to about 1.5 percent cross-linking agent substantially free from polyalkenyl polyether, with the percentages being based upon the weights of the unpolymerized repeating unit and cross-linking agent, respectively. In more preferred practice, at least about 90 percent of the repeating units contain at least one carboxyl functionality, and in still more preferred practice, at least 95 percent of those repeating units contain at least one carboxyl functionality. Most preferably, this material is a reaction product of the polymerization of only a carboxyl-functional monomer and a cross-linking agent. Also in more preferred practice, this component contains about 0.1 to about 1 percent by weight of polymerized cross-linking agent. The material also contains from 5% to 25%, preferably 18% to 22% calcium as a calcium salt of the polymer acid. Certain species of this type of polymer is commercially available under the generic name "calcium polycarbophil".

A calcium polycarbophil type composition polymer useful herein may thus be defined as a reaction product of the copolymerization of at least 80 weight percent monoethylenically unsaturated carboxy-functional monomer and about 0.05 to about 1.5 weight percent of a cross-linking agent free of polyalkenyl polyether and 18-22% of calcium. The remaining monomers that may be present to constitute 100 percent by weight of the monomers.

In addition to the above two ingredients, the polycarbophil type polymer may also include polymerized monoethylenically unsaturated repeating units such as C1-C6 alkyl esters of one or more of the above-described acids such as hexyl acrylate, butyl methacrylate and methyl crotonate; hydroxyalkylene-functional esters of the above-described acids that contain a per molecule average of 1 to about 4 oxyalkylene groups containing 2-3 carbon atoms such as hydroxyethyl methacrylate, hydroxypropyl acrylate and tetraethylene glycol monoacrylate; methacrylamide, acrylamide and their C1-C4 mon- and di-alkyl derivatives such as N-methyl acrylamide, N-butyl methacrylamide and N,N-dimethyl acrylamide; styrene; and the like as are known in the art as being copolymerizable with the above described carboxyl functionality-containing monomers and cross-linking agents. The polymers most preferably are prepared from only the monoethylenically unsaturated carboxy-functional monomer and the cross-linking agent.

The calcium polycarbophil type composition useful herein may be prepared by conventional free radical polymerization techniques utilizing initiators such as benzoyl peroxide, azobisisobutyronitrile, and the like, are polymerized in an aqueous medium, and are not agglomerated by steam action. A particularly preferred polycarbophil component that is commercially available is that material sold under the designation calcium polycarbophil by the B. F. Goodrich Co. of Cleveland, Ohio. The United States Pharmacopeia, 1990 edition, United States Pharmacopeial Convention, Inc., Rockville, Md., at page 218, indicates that calcium polycarbophil is a calcium salt of polyacrylic acid cross-linked with divinyl glycol that has a calcium content of not less than 18% and not more than 22% and absorbs not less than 35 grams of sodium bicarbonate solution per one gram of the powder in the test under Absorbing power.

The polycarbophil component preferably is present in the form of its calcium salt. The divalent cation should be present in an amount from about 5 to about 25 percent and preferably from about 18 to about 22 percent, based on the weight of polycarbophil. Most preferably, the calcium cation is originally present as the salt of the polycarbophil type composition. However, it may also be otherwise introduced as a calcium ion-containing compound, such as calcium chloride, calcium gluconate. calcium hydroxide, or the like.

Calcium polycarbophil has been known heretofore and has been primarily employed as a bulk laxative, requiring the ingestion of large quantities of calcium polycarbophil, such as from about 0.625 to about 1.25 grams per dose, taken in 1 to 3 doses per day. The quantity of polycarbophil employed for purposes of appetite suppression in accordance with the present invention is much smaller, from about 0.010 to about 0.400 grams per dose, taken 1 to 3 times per day. Hence, the amount of polycarbophil administered in accordance with the present invention is less than the amount of polycarbophil necessary to induce a laxative effect. Typically the amount of polycarbophil ingested at one time will be from about 0.050 to about 0.400 grams and usually from about 0.100 to about 0.300 grams. Typically, the dose will be taken prior to meals.

The timing of the administration of the polycarbophil is not critical and can be taken based upon individual needs. For example, the polycarbophil can be taken when a feeling of hunger occurs or on a schedule, such as at least once per day or at least twice per day. It may be beneficial to administer the polycarbophil based upon the timing of meals. By taking the polycarbophil before a meal, such as from about one-quarter of an hour to two hours, preferably from about one-half to about three-quarters of an hour before a meal, the appetite may be sufficiently depressed that a smaller than normal quantity of food may be ingested, as the polycarbophil will act to curb the appetite. Typically, then, the polycarbophil will be taken some time period prior to a meal, or at the time a usual meal is eaten, eliminating the meal altogether, as the polycarbophil can provide a sufficient feeling of satiation to eliminate some normally eaten meals.

The polycarbophil can be administered in any form suitable for oral administration. Generally the polycarbophil will be in the form of calcium polycarbophil which is in the form of a lozenge, chewable tablet, powder, or ingestible tablet. Each such dosage form will typically contain from about 0.010 to about 0.500 gram of calcium polycarbophil. The dosage forms may be essentially all polycarbophil or they may contain other ingredients, such as flavoring agents, colorants, artificial sweeteners, and the like.

The polycarbophil can be incorporated into the desired dosage form by any suitable means. For example, calcium polycarbophil may be mixed, if desired, with other excipients and active agents, and mixed with water and other cosolvents, granulated, dried to a desired initial dry weight moisture content and tableted using conventional tableting procedures. The resultant products may be molded into lozenges, or gums, for example; encapsulated into gelatin capsules; compressed into tablets; ground into dry powders or granules and may be further coated, if desired.

An auxiliary hydrocolloid may be employed, such as cellulose polymers which are cellulose ethers such as methyl cellulose, cellulose alkyl hydroxylates such as hydroxypropylmethyl cellulose, hydroxypropyl cellulose, hydroxymethyl cellulose or hydroxyethyl cellulose, cellulose alkyl carboxylates such as carboxymethyl cellulose and carboxyethyl cellulose, and alkali metal salts of cellulose alkyl carboxylates, such as sodium carboxymethyl cellulose and sodium carboxyethyl cellulose, as well as carboxypolymethylene (molecular weight 2.5 to 3.5 million), gum acacia, guar gum, gum tragacanth, gum xanthan, alkali metal or alkaline earth metal caragenates, and alginates, such as alginic acid, ammonium or sodium alginate or mixtures thereof. Simple or complex carbohydrates or polyols, such as sucrose, xylose, mannitol, glucose, starch, Pluronic surfactants, and the like may also be employed to modify the hydrogel structure.

The polycarbophil compositions used in accordance with the present invention may include an additional active agent in an amount within the range of from about 0.0001 to about 65% by weight, preferably in an amount within the range of from more than 0.001 to about 35% by weight of the composition. The calcium polycarbophil polymer will be present in an amount within the range of from about 0.1 to about 99%, and preferably from about 0.25% to about 50% by weight of the composition; and the auxiliary excipients may be present in an amount within the range of from about 0.01 to about 99%, and preferably from about 0.25 to about 50% by weight of the composition. Water or other suitable solvents may typically be present in an amount of about 0.5 to about 200% and preferably from about 0.1% to about 100%, based upon the weight of the calcium polycarbophil. The amount of water and cosolvents added may vary depending upon whether other excipients are present. The water content as described herein is the amount added to initiate the formation of a hydrogel. Once the gel is formed, the water and/or cosolvent may be removed to obtain a dry powder, granules or a matrix, or more water may be added to obtain the desired consistency. In an alternative method, the compositions may be prepared without use of any solvent or cosolvent by direct incorporation of other excipients.

The compositions may optionally include additional edible non-toxic ingredients as conventionally employed in medicinal dosage forms. Thus, the compositions of the invention may optionally include one or more excipients in an amount within the range of from about 0.1% to about 99% by weight and preferably from about 1% to about 95% by weight, such as lactose, sugar, corn starch, modified corn starch, mannitol, sorbitol, and inorganic salts such as calcium carbonate. Other conventional ingredients which may optionally be present include preservatives, stabilizers, plasticizers, cosolvents, anti-adherents or silica flow conditioners or glidants, such as Syloid brand silicon dioxide as well as FD&C colors.

The dosage form can be packaged in unit dose blister packs, pouches in a carton, vials with screw or flip-top lids, bottles with screw or flip-top lids, or any other convenient package form.

The present invention will be further described through the following nonlimiting examples.

EXAMPLE 1

A lozenge containing calcium polycarbophil was formulated in the following manner.

Calcium Polycarbophil, USP (Carbopol EX-83 Resin, Lot No. Z139117, B.F. Goodrich) is used in this example. Other grades of varying particle size and surface area materials of this resin may be used to obtain other desirable properties.

Twenty-five grams of calcium polycarbophil, USP, 443.50 grams of anhydrous lactose, USP, and 25.0 grams of sodium alginate (Keltone HV), are thoroughly mixed. The resultant mass is granulated with a suitable granulating fluid and the wet mass is then passed through a granulating mill, equipped with a suitable screen. The wet mass is dried to a specified moisture level and then passed through a granulating mill equipped with an appropriate screen. Suitable flavoring agents, artificial sweeteners and lubricants are added to the dried granules. The product is then compressed to produce tablets of about 2 to about 2.5 grams, total weight, using a three-quarter inch size flat face, beveled edge round tooling.

EXAMPLE 2

The lozenge of Example 1 was administered to a subject as follows.

The Subject R took one lozenge about 5 P.M. every evening for four consecutive days. Each lozenge was sucked for about 30–40 minutes. It was noted by the subject that appetite was reduced significantly and no hunger feeling was present for several hours after use of the lozenge. The subject had the sensation that a full meal had been taken. No adverse or unpleasant findings were noted and the subject did not notice any other effects. No bulk laxation was noted during this time.

EXAMPLE 3

The Subject H took the preparation of Example 1, one lozenge every day at about 11:30 A.M. for four days. The subject also reported that the lozenge induced a feeling as if the subject was not hungry. The subject took lunch about 40 to 50 minutes after taking the lozenges the subject indicted that appetite was significantly lowered and that smaller than usual quantity of lunch were consumed. No adverse effects or laxation was reported by this subject.

From the foregoing Examples 2 and 3, it has been demonstrated that the lozenge formulation containing as its main component polycarbophil exhibits appetite suppressant activity and induces a feeling of satiation. It is not understood through what mechanism the results are achieved, but it has been demonstrated through the foregoing Examples 2 and 3 that polycarbophil has a significant direct effect upon appetite and hunger.

What is claimed is:

1. A method for suppressing appetite in a subject comprising administering polycarbophil by mouth to the subject in an amount of about 0.010 to about 0.500 gram which is effective to suppress the appetite of the subject without inducing a laxative effect in the subject.

2. The method of claim 1 wherein the polycarbophil is administered as calcium polycarbophil.

3. The method of claim 1 wherein the polycarbophil is administered from about 0.25 to about 2.0 hours before a meal.

4. The method of claim 3 wherein the polycarbophil is administered at least one dose before each meal.

5. The method of claim 3 wherein the polycarbophil is administered at least twice per day.

6. The method of claim 2 wherein the polycarbophil is administered in the form of a chewable tablet.

7. The method of claim 4 wherein the polycarbophil is administered in the form of a chewable tablet.

8. The method of claim 2 wherein the polycarbophil is administered in the form of an ingestible tablet.

9. The method of claim 4 wherein the polycarbophil is administered in the form of an ingestible tablet.

10. The method of claim 2 wherein the polycarbophil is administered in the form of a powder.

11. The method of claim 4 wherein the polycarbophil is administered in the form of a powder.

12. The method of claim 3 wherein the polycarbophil is administered as often as needed to overcome the feeling of hunger.

13. The method of claim 2 wherein the polycarbophil is administered in the form of a lozenge.

14. The method of claim 4 wherein the polycarbophil is administered in the form of a lozenge.

* * * * *